(12) United States Patent
Cao et al.

(10) Patent No.: US 9,846,149 B2
(45) Date of Patent: Dec. 19, 2017

(54) LUBRICANT HEALTH AND SERVICE DETERMINATION

(71) Applicant: Ingersoll-Rand Company, Davidson, NC (US)

(72) Inventors: Ming Cao, Glastonbury, CT (US); David Cowley, Charlotte, NC (US); Mike Lukavsky, Huntersville, NC (US)

(73) Assignee: Ingersoll-Rand Company, Davidson, NC (US)

( * ) Notice: Subject to any disclaimer, the term of this patent is extended or adjusted under 35 U.S.C. 154(b) by 200 days.

(21) Appl. No.: 14/463,418

(22) Filed: Aug. 19, 2014

(65) Prior Publication Data

US 2015/0047419 A1 Feb. 19, 2015

Related U.S. Application Data

(60) Provisional application No. 61/867,490, filed on Aug. 19, 2013.

(51) Int. Cl.
| | |
|---|---|
| *G01N 33/26* | (2006.01) |
| *G01N 33/28* | (2006.01) |
| *F04B 39/02* | (2006.01) |
| *F01M 11/10* | (2006.01) |
| *F16N 7/40* | (2006.01) |

(52) U.S. Cl.
CPC ......... *G01N 33/2888* (2013.01); *F01M 11/10* (2013.01); *F04B 39/02* (2013.01); *F01M 2011/14* (2013.01); *F01M 2011/1406* (2013.01); *F01M 2011/1493* (2013.01); *F16N 7/40* (2013.01); *F16N 2200/02* (2013.01); *F16N 2200/08* (2013.01); *F16N 2250/18* (2013.01)

(58) Field of Classification Search
CPC ................................ F16N 29/04; G01N 33/30
USPC ........................................................ 73/53.07
See application file for complete search history.

(56) References Cited

U.S. PATENT DOCUMENTS

| | | | |
|---|---|---|---|
| 3,981,584 A | 9/1976 | Guymer | |
| 4,169,677 A | 10/1979 | Luria | |
| 5,586,161 A | 12/1996 | Russell et al. | |
| 5,604,441 A | 2/1997 | Freese et al. | |
| 6,286,363 B1 | 9/2001 | Discenzo | |
| 6,732,572 B1 | 5/2004 | Pickert et al. | |
| 6,949,936 B2 | 9/2005 | Stone et al. | |
| 7,259,017 B2 | 8/2007 | Kawabata et al. | |
| 7,581,434 B1 * | 9/2009 | Discenzo | G01N 33/2888 73/53.01 |
| 2006/0267600 A1 * | 11/2006 | Beatty | C10G 25/003 324/698 |

(Continued)

OTHER PUBLICATIONS

Polaris Laboratories, How to Take an Oil Sample, Technical Bulletin, 2008, 3 Pages, Polaris Laboratories.

*Primary Examiner* — Benjamin Schmitt
(74) *Attorney, Agent, or Firm* — Taft Stettinius & Hollister LLP (57) ABSTRACT

A method is disclosed that includes determining a current level of a plurality of lubricant parameters present in a portion of lubricant, comparing the current level of each of the plurality of lubricant parameters to a threshold value corresponding to each of the plurality of lubricant parameters, analyzing a priority of each of the lubricant parameters, and determining a health status of the lubricant in response to the comparing and the analyzing.

19 Claims, 6 Drawing Sheets

(56) References Cited

U.S. PATENT DOCUMENTS

| | | |
|---|---|---|
| 2007/0074563 A1 | 4/2007 | Liu et al. |
| 2010/0299080 A1 | 11/2010 | Willmann et al. |
| 2013/0197738 A1* | 8/2013 | Dvorak .............. G01N 33/2858 701/29.5 |
| 2014/0019068 A1* | 1/2014 | Schneider .......... G01N 33/2888 702/30 |

* cited by examiner

LUBRICANT HEALTH AND SERVICE DETERMINATION

CROSS REFERENCE TO RELATED APPLICATIONS

The present application claims the benefit of U.S. Provisional Patent Application 61/867,490 filed Aug. 19, 2013, the contents of which are incorporated herein by reference in their entirety.

FIELD OF THE INVENTION

The present invention generally relates to lubricants, and more particularly, but not exclusively, to the determination of a lubricant health.

BACKGROUND OF THE INVENTION

Lubricant diagnostics remains an area of interest. Many current lubricant diagnostics require frequent maintenance services to be performed. Maintenance services which are performed at too great a frequency can result in excessive machine downtime and lubricant waste. Therefore, further technological developments are desirable in this area.

BRIEF SUMMARY OF THE INVENTION

One embodiment of the present invention is a unique lubricant health status determination. Other embodiments include apparatuses, systems, devices, hardware, methods, and combinations for determining lubricant health, life, and service actions to be performed. Further embodiments, forms, features, aspects, benefits, and advantages of the present application shall become apparent from the description and figures provided herewith.

BRIEF DESCRIPTION OF THE SEVERAL VIEWS OF THE DRAWINGS

The description herein makes reference to the accompanying figures wherein like reference numerals refer to like parts throughout the several views, and wherein.

DETAILED DESCRIPTION OF THE INVENTION

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
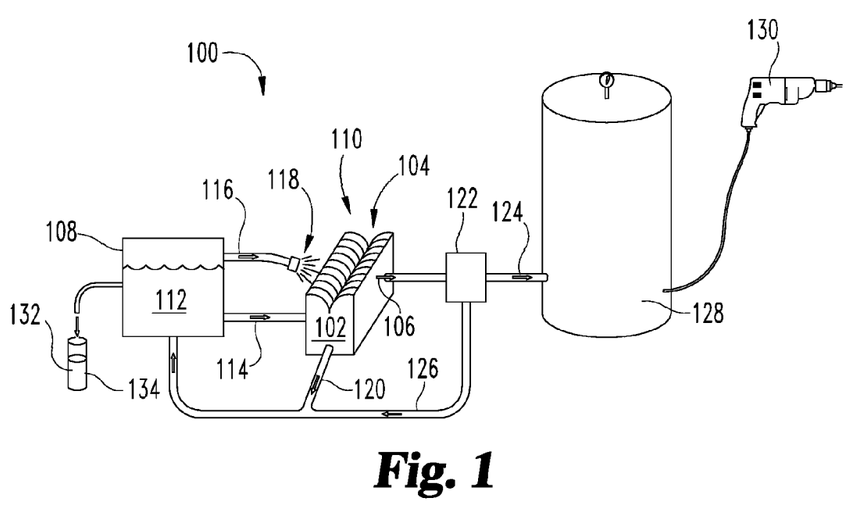
FIG. 1 depicts an embodiment of a sample of lubricant being taken from a system requiring lubrication.

FIG. 1 illustrates a system 100 which uses a lubricant 112. The exemplary system 100 includes an air compressor 102 which compresses ambient air 110. The air compressor 102 can be of a rotary configuration, a centrifugal configuration, and/or of a screw type including a plurality of lobes 104. The lubricant 112 can be stored in a tank 108 to be flowed to the compressor such as through flowpaths 114 and 116. The lubricant 112 can be utilized for many applications including being provided to other moving components within the air compressor 102, including, but not limited to bearings, transmissions, gear assemblies, various rotating components, and the like.

The compressed air 106 can include a fraction of lubricant 112. An air/lubricant separator 122 can be utilized to separate the lubricant 112 from the compressed air 124. The air compressor 102 can provide compressed air 124 to compressed air storage tank 128 to be utilized by an air driven motor, such as in pneumatic tool 130. The lubricant 112 can be returned via flowpath 126 to the lubricant storage tank 108. A flowpath 120 can additionally and/or alternately be utilized to return the lubricant 112 from a sump portion, or other return area, of the compressor 102 to the lubricant storage tank 108.

During use, the lubricant 112 can be exposed to heat, air, water (e.g. from condensate and/or heat exchangers), and particulate from the wear surfaces associated with relative components in or with the compressor 102. A sample 132 of lubricant 112 can be taken from the system 100, potentially from the lubricant 112 storage tank 108 or any other suitable location, to be tested. The lubricant 112 includes a plurality of lubricant parameters 134. Some of the lubricant parameters 134 are found in fresh, bulk lubricant, but the properties of which can be altered during use. Other lubricant parameters 134 can be added through use, such as the introduction of particulate through wear.

While the system 100 illustrates an air compressor 102, the present application is not intended to be limited thereto. The application encompasses any machinery 102 which utilizes a lubricant 112 for a variety of purposes, including, but not limited to friction reduction, heat reduction or transfer, sealing properties, and increased component life. The machinery 102 can include compressors, pumps, engines, or any other devices which utilize a lubricant 112. The lubricant 112 can include petroleum based oils, various synthetically derived oils, esters, silicones, or any other suitable fluid which can act as a lubricant 112.

The lubricant parameters 134 can include a lubricant viscosity, a total acid number (TAN), a total base number (TBN), an oxidation level, a water content, and a pH level. The lubricant parameters 134 can include additives which have been added to the lubricant 112 to reduce friction, modify viscous properties of the lubricant 112 (e.g. improving a viscosity index, increasing viscosity resistance to thermal breakdown, etc.), increase a resistance to corrosion and oxidation, to aid in the prevention of aging and/or contamination, and can include any other additives to modify a property of the lubricant 112. The lubricant parameters 134 can additionally include particulate in the lubricant 112. Additionally, the lubricant parameters 134 can include any lubricant property which can be sensed, measured, determined in response to a lubricant analysis, etc., that can affect a health of the lubricant 112 or a health or life of the machinery 102.

Figure 2A:
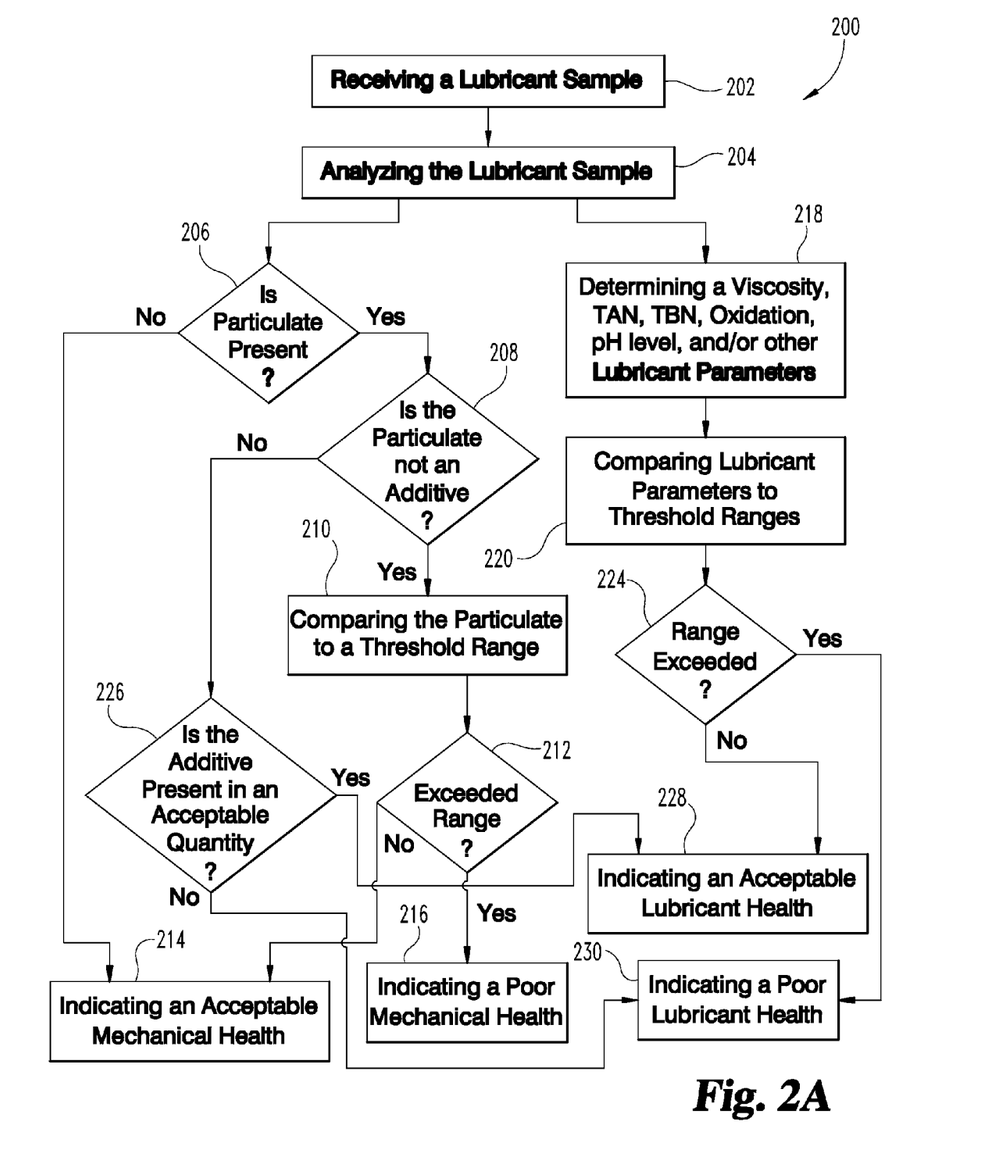
FIG. 2A depicts an illustrative flow diagram of one embodiment of determining a lubricant health and a mechanical health for a lubricated system.

FIG. 2A depicts an illustrative process 200 for determining a health of a lubricant 112 and the machinery 102 which utilizes the lubricant 112. At 202, a sample of lubricant is received by a lab, an in house analysis, a plurality of sensing devices which can be incorporated into the machinery 102 or the storage tank 108, and/or any other person or device capable of performing a lubricant analysis. The lubricant sample can be drawn during a routine maintenance schedule. An analysis is performed of the lubricant sample at 204. The analysis can be performed utilizing gas chromatography, infrared spectroscopy, metallic separation and elemental analysis, and/or any other method of determining a lubricant content or level of various lubricant parameters 134, as is desired for a specific application.

At 206, a determination is made as to whether particulate is present in the lubricant 112. If no particulate is present, an acceptable mechanical health can be indicated at 214. If particulate is present, at 208 it is determined if the particulate is not an additive. If the particulate is not an additive, the particulate content is compared to a threshold range at 210. At 212 it is determined if the threshold range is exceeded. If the threshold range is not exceeded, at 214 an acceptable mechanical health can be indicated. If the threshold range is exceeded, a poor mechanical health can be indicated at 216.

The threshold range can include one or more values or limits which are predetermined, such that a determination can be made as to a mechanical health of the machinery 102 when a particulate determined from the lubricant analysis is compared to the threshold range. The particulate can include a total particulate count, a particulate count of metallic particles, a particulate count of an individual type of metal, a particulate size of the total particulate or a particulate size of an individual element, or the like. For example, if a portion of the machinery 102 is constructed of steel, a steel particulate count can be attributed to wear of the specific portion of the machinery 102 which is constructed of steel. In this specific example, during each service interval an acceptable range of steel particulate, a maximum level of steel particulate, or an increase in the steel particulate within the lubricant 112 can be predetermined based upon acceptable normal wear of the machinery 102. If the steel particulate count exceeds or falls outside of the acceptable range, level, or increase, a the mechanical health can be indicated as poor at 216.

The amount a particulate count falls outside of the particulate threshold range can also be utilized as a diagnostic tool. For example, if the particulate count, level, etc. only minimally falls outside the threshold range, then a minimal severity may be assigned to the mechanical health. On the other hand, if the particulate count falls further outside the threshold range a critical severity may be assigned to the mechanical health. The indication of mechanical health can notify a technician that a specific service needs to be performed, and additionally the indication can include information that can be useful during a mechanical diagnosis of the machinery 102.

In response to the lubricant analysis, a number of lubricant parameter 134 values, levels, etc. are determined at 218. At 220, the lubricant parameters are compared to threshold ranges. The threshold ranges can be a single value, a plurality of values, a level, an increase in a parameter value since a previous lubricant analysis, or any other type of predetermined range against which a lubricant parameter 134 value can be compared in order to determine a lubricant health. If one or more lubricant parameters 134 fall outside of the threshold range or ranges at 224, a poor lubricant health can be indicated at 230. If the lubricant parameters do not fall outside the threshold range or ranges, an acceptable lubricant health can be indicated at 228. As was aforementioned with regard to the particulate range, the amount a lubricant parameter exceeds or falls outside of a threshold range can be utilized when determining a lubricant health or lubricant health severity level.

As was previously discussed, the lubricant 112 can include a number of additives, that would be present in fresh lubricant prior to use. If the particulate is determined to be an additive at 208, then at 226 it can be determined if the additive is present in an acceptable quantity. If the additive is present in an acceptable quantity, an acceptable lubricant health can be indicated at 228. If the additive is not present in an acceptable quantity, a poor lubricant health can be indicated at 230. An acceptable quantity of a particular lubricant additive can be determined in response to a number of factors including the type of lubricant 112 utilized, the specific application for which the lubricant 112 is utilized, any decrease or increase in an amount of a specific lubricant additive during use of the machinery 102, the amount of a particular additive relative to other substances in the lubricant 112 (e.g. an anti-corrosion additive compared to the TAN), or any other factors which may be utilized to determine if an additive is present in an acceptable quantity in the lubricant 112.

Figure 2B:
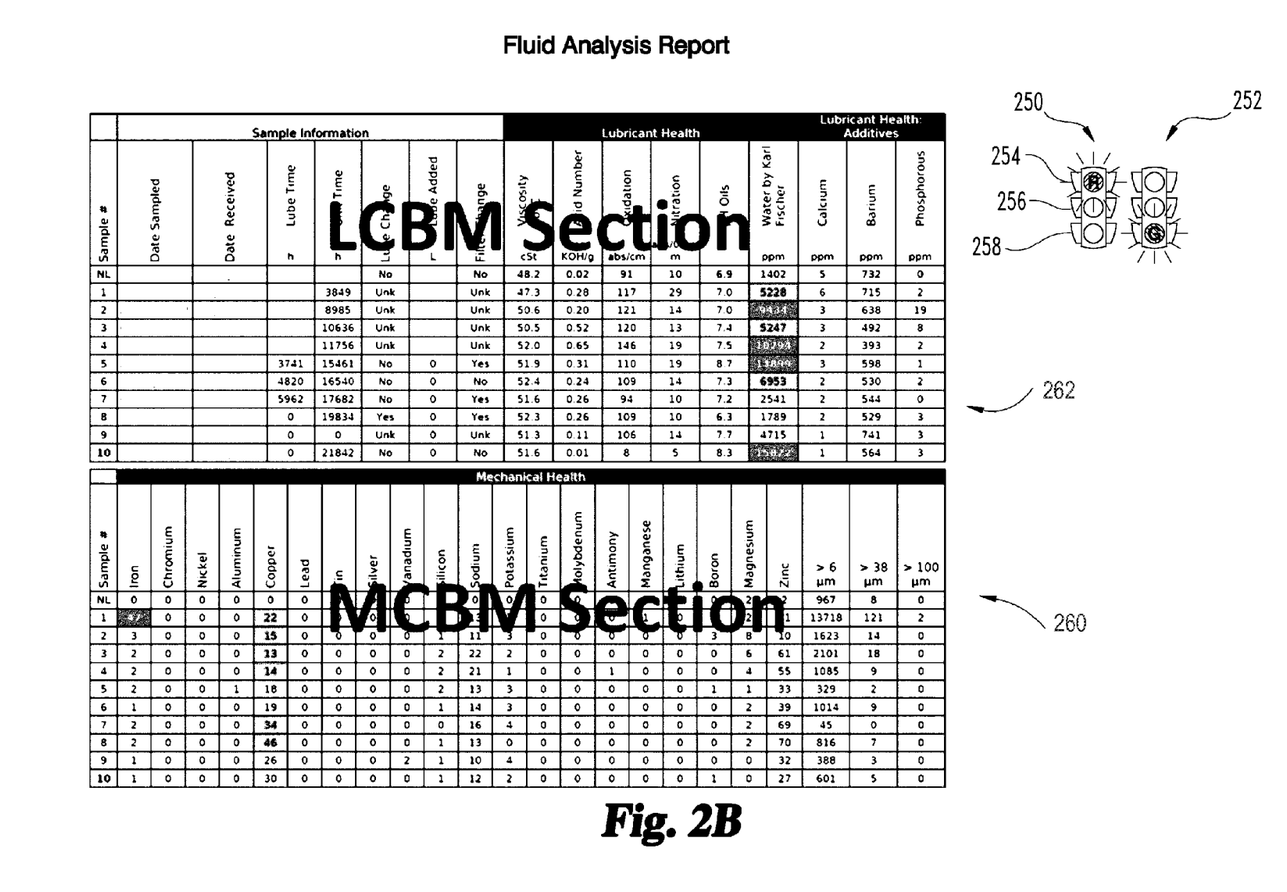
FIG. 2B depicts an illustrative differentiation between a lubricant health status and a mechanical health status.

As is illustrated, the mechanical health and the lubricant health can be indicated separately. Separation of the lubricant health and the mechanical health can allow a technician presented with the analysis report to readily identify if a service interval needs to be recalculated (or already has been recalculated as part of the report), if a specific parameter 134 needs to be closely monitored, if a particular service needs to be performed, and whether the service, problem, area of monitoring etc. is associated with the lubricant 112 or the machinery 102. Referring now to FIG. 2B, a lubricant analysis report illustrates the separation in lubricant condition based monitoring (LCBM) 262 and mechanical condition based monitoring (MCBM) 260.

A lubricant health indicator can be color coded, for example through the use of stop light type indicators 250 MCBM and 252 LCBM. Green 254, used in association with mechanical health, can imply a first severity (e.g. that a particulate count falls within acceptable levels). Yellow 256, used in association with mechanical health, can imply a second severity (e.g. that a particulate count falls at or slightly above acceptable levels or falls within acceptable levels, but near a high end of acceptability). Red 258, used in association with mechanical health, can imply a third severity (e.g. that a particulate count falls outside acceptable levels and/or that a service is immediately required). As illustrated, lubricant health can also use the same indication scheme. While various color indicators were illustrated to indicate a health status of a lubricant 112 or a mechanical health status, the present application is not be limited thereto. Shapes, various signal indicators, alpha numeric codes, and/or any other indicators can be utilized to indicate a health status.

Figure 2C:
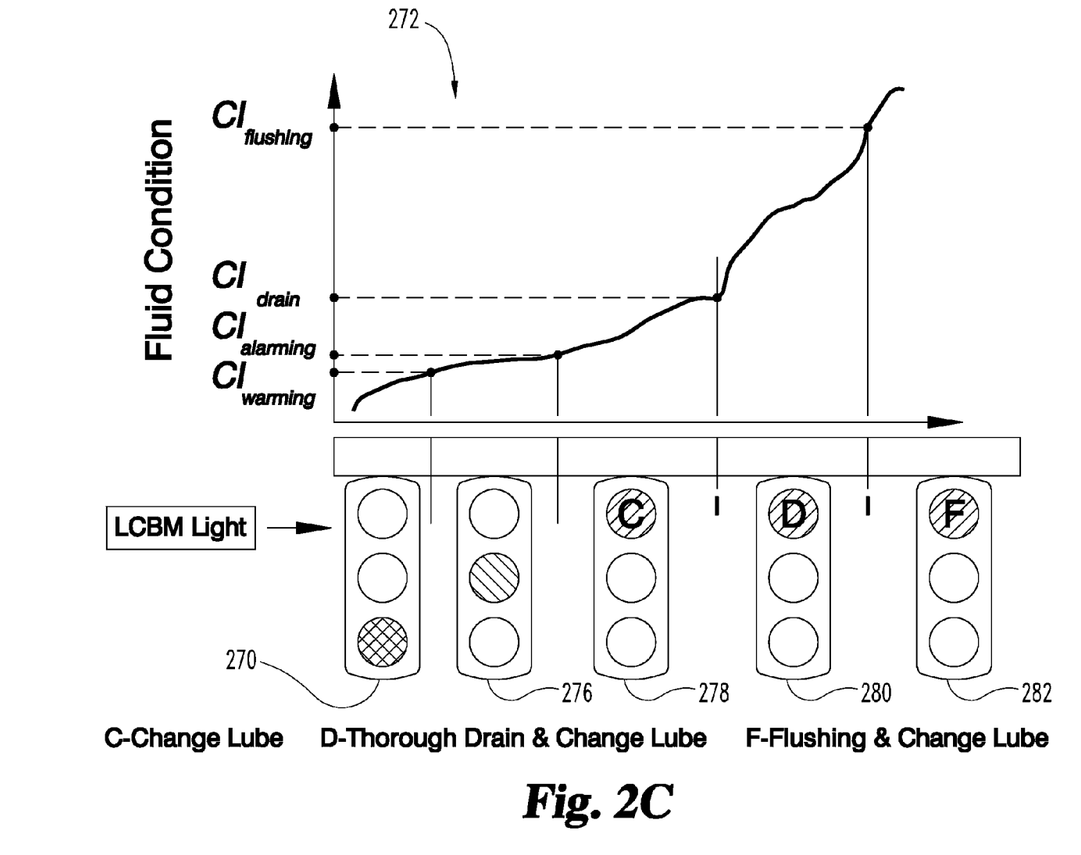
FIG. 2C depicts illustrative service decisions presented corresponding to a lubricant health status.

FIG. 2C illustrates an embodiment including a plurality of lubricant severity levels and service actions to be performed, in response to a health analysis of the lubricant 112. At 272, the health of the lubricant 112 is charted as a severity level of the lubricant 112 corresponding to predetermined maintenance service points (e.g. when the severity of the lubricant reaches a predetermined level, a specific service is to be performed). A green light can illustrate a first severity 270 lubricant condition. If a first severity 270 lubricant condition is indicated, no service action is indicated and a service interval can be extended in some instances. If a second severity 276 lubricant condition is indicated, the lubricant may not necessitate action at the present time; however, the lubricant condition can be monitored and/or a service interval can be decreased. If a third severity 278, 280, 282 lubricant condition is indicated, a maintenance action can be indicated. A lowest third severity 278 can indicate that the lubricant 112 should be changed. A medium third severity 280 can indicate a thorough drain and lubricant change. The highest third severity 282 can indicate a flush and lubricant change are recommended. A lubricant health indication scheme including colors or various sign indication can allow a technician to readily ascertain a health status and can further indicate any action which can be taken in response thereto (e.g. through an alphanumeric code as illustrated or through any other indication as previously described).

Figure 3:
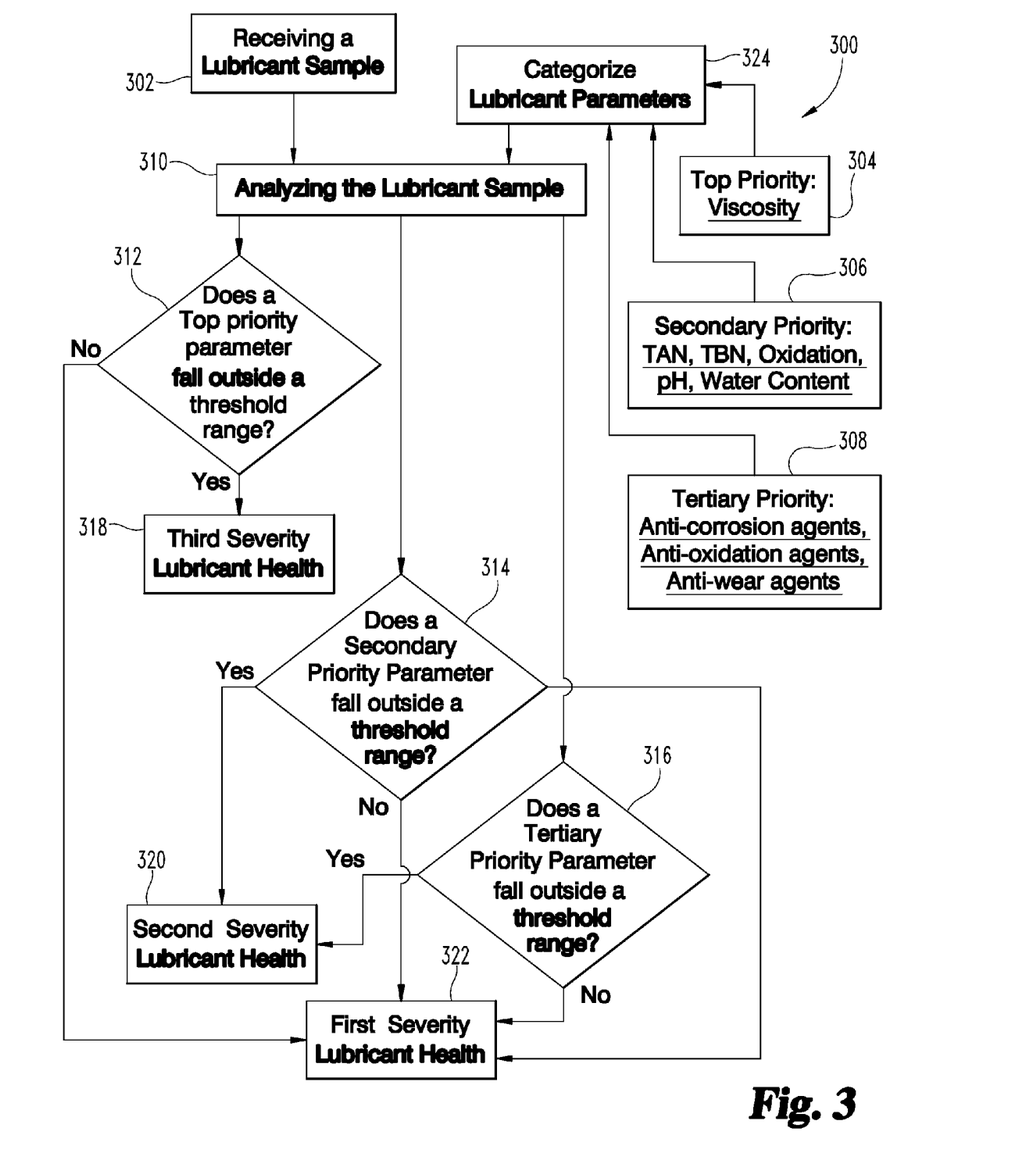
FIG. 3 depicts an illustrative flow diagram of one embodiment of determining a lubricant health status.

Referring to FIG. 3, a process 300 is disclosed for determining a lubricant health severity. At 302 the lubricant sample 132 is received. The plurality of lubricant parameters 134, as were previously described, are categorized at 324. Each lubricant parameters 134 can be categorized based upon a criticality of the specific lubricant parameter.

A criticality of a lubricant parameter 134 can be determined based upon the specific application for which the lubricant 112 is utilized. An effect the lubricant parameter 134 has upon the overall performance of the lubricant 112 or upon wear of the machinery 102 can be utilized to determine a criticality of the lubricant parameter 134. For example, a lubricant viscosity can be categorized as a first priority as the viscosity of the lubricant can affect the ability of the lubricant 112 to flow; and, therefore the ability of the lubricant to carry other lubricant parameters 134. Criticalities of lubricant parameters 134 can also be determined in relation to a specific lubricant 112 performance factor. To demonstrate one non-limiting example, an anti-corrosion agent may be listed as a secondary priority while a TAN or TBN can be listed as a first priority. In this instance, although the anti-corrosion agent may fall outside of an acceptable threshold range, so long as the TAN or TBN falls within an acceptable threshold range, the overall lubricant health can be deemed acceptable.

The number of priority or criticality groups can be application specific. In some forms, a first priority group and a second less critical priority group can be utilized. In other forms, a third priority group can be added, the third priority group being less critical than the second priority group. It is contemplated that any number of lubricant priority groups can be utilized depending upon the specific application and a desired number of distinctions between lubricant parameters 134.

A lubricant viscosity can be categorized as a first (top) priority at 304. The TAN, TBN, oxidation, PH, and water content can be categorized as secondary priorities, as illustrated at 306. A plurality of additives, including anti-corrosion agents, anti-oxidation agents, and anti-wear agents can be categorized as a tertiary priority at 308.

The lubricant sample 132 is analyzed at 310. If a first or top priority parameter 134 exceeds a threshold value or falls outside of a threshold range at 312, the lubricant health can be assigned a third severity 318. If the first priority lubricant parameter 304 does not exceed the threshold value or fall outside the threshold range at 312, the lubricant health can be assigned a first severity at 322.

At 314 it is determined if a secondary priority parameter 306 exceeds a threshold value or falls outside of a threshold range. If the secondary priority parameter 306 does exceed the threshold value or falls outside the threshold range, the lubricant health can be assigned a second severity at 320. If the secondary priority parameter does not exceed the threshold value or fall outside the threshold range, the lubricant health can be assigned a first severity at 322.

At 316 it is determined if a tertiary priority parameter 308 exceeds a threshold value or falls outside of a threshold range. If the tertiary priority parameter 308 does exceed the threshold value or fall outside the threshold range, the lubricant health can be assigned a second severity at 320. If the tertiary priority parameter 308 does not exceed the threshold value or fall outside the threshold range, the lubricant health can be assigned a first severity at 322. In some forms, even if the tertiary priority parameter 308 does exceed the threshold value or falls outside the threshold range, the lubricant health can be assigned a first lubricant health severity 322, as the criticality of the tertiary priority parameter 308 can have a low importance relative to the higher priority categories.

When the term "exceed" is used with respect to a threshold value, it should be understood that "exceed" can be defined as describing a measured value that is below a minimum desired threshold value or alternatively a measured value that is above a maximum threshold value. The present application further contemplates that a lubricant parameter 134 falling below a threshold value can also adversely affect the lubricant health. Therefore, a lubricant parameter 134 falling below a threshold value can trigger one or more severity conditions.

Figure 4:
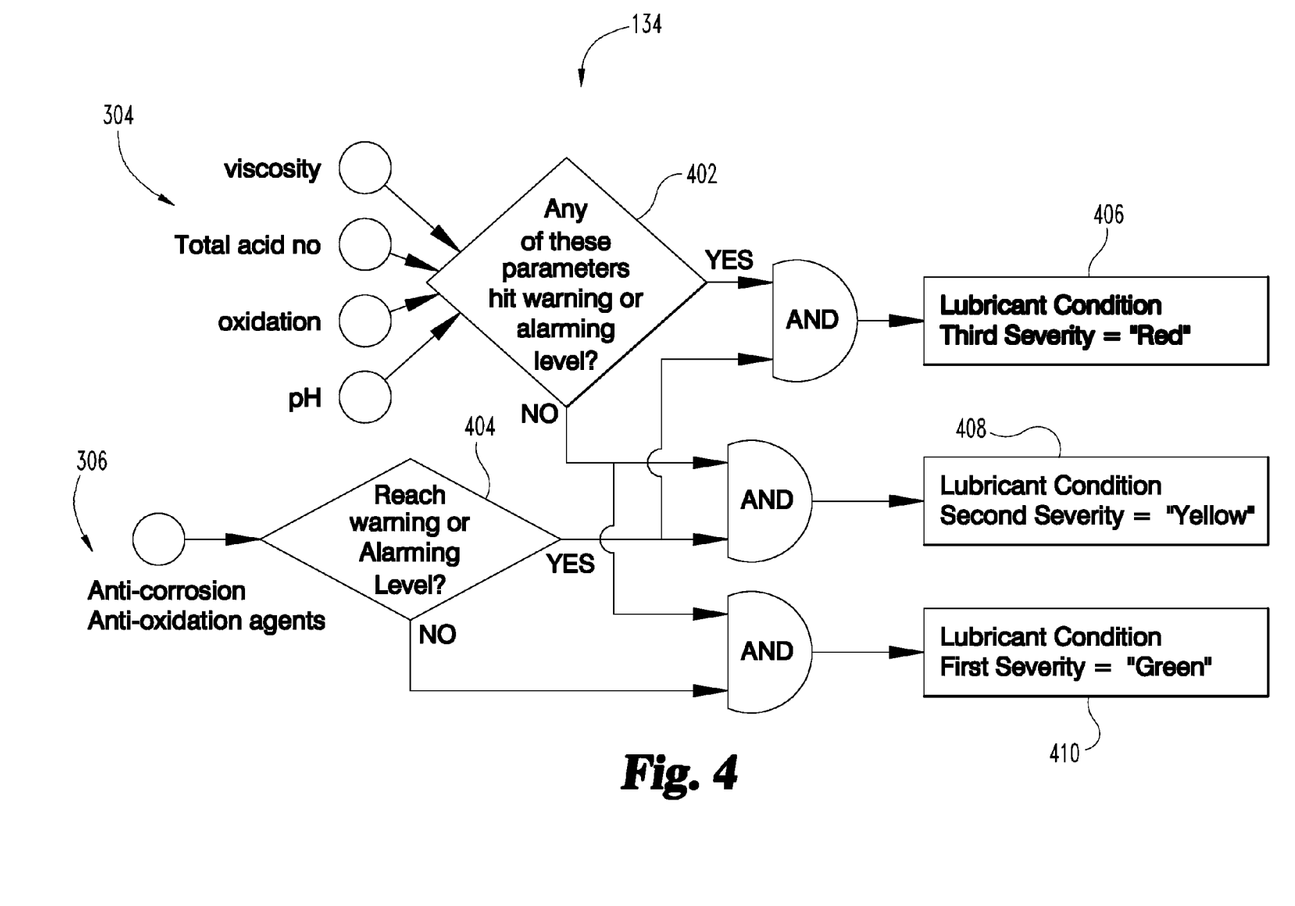
FIG. 4 depicts an illustrative procedure of an embodiment for determining a lubricant health status.

Referring now to FIG. 4 another example of a process for determining a lubricant health is illustrated. A plurality of lubricant parameters 134 are grouped into a first priority group 304 and a second priority group 306. In this example, the first priority group 304 includes viscosity, TAN, oxidation, and pH. The second priority group 306 includes anti-corrosion and anti-oxidation agents. It is determined at 402 if any of the first priority group 304 lubricant parameters 134 are at a warning or an alarm level. At 404, it is determined if any of the second priority group 306 lubricant parameters 134 are at a warning or an alarm level. The warning or alarm level can be determined in response to a comparison between a threshold value or range as was aforementioned. If none of the lubricant parameters 134 are at a warning or alarm level, the lubricant health is indicated as a first severity at 410. If none of the first priority group 304 lubricant parameters 134 are at a warning or alarm level but at least one of the lubricant parameters in the second priority group 306 has reached a warning or alarm level, the lubricant health is indicated as a second severity at 408. If at least one lubricant parameter 134 from each of the first priority group 304 and the second priority group 306 are at a warning or alarm level, the lubricant health is indicated as a third severity at 406.

The lubricant health, or severity, can be utilized to determine a service interval schedule, a useful service life of the lubricant 112, a service to be performed, and/or if any additives should be added to the lubricant 112. The lubricant health for a specific machine 102 can be extrapolated to determine a maintenance schedule or useful lubricant service life for a plurality of machines which operate under similar conditions. Data from a lubricant health report of a specific machine can be utilized, along with other variables including machine size, speed, and/or other variables which can affect lubricant health, to determine the maintenance schedule or useful lubricant service life for other machines and/or for the machine 102.

In one aspect the present disclosure includes a method, comprising categorizing lubricant parameters into a plurality of priority groups, wherein the priority groups are determined in response to a criticality of the lubricant parameters on at least one of a lubricant performance and a component life; analyzing a sample of lubricant; assigning an indicator value to each of the lubricant parameters in response to the analyzing; comparing the indicator values to predetermined threshold values; and determining a health status in response to the comparing and the priority groups corresponding to the lubricant parameters.

In refining aspects the method includes the threshold value is a threshold range, determining at least one of a maintenance service, a maintenance schedule, and a remaining useful lubricant life in response to the health status; wherein determining the health status further includes determining a lubricant health status and a mechanical health status, the lubricant health status being independent of the mechanical health status; wherein determining the mechanical health status further includes categorizing a particulate count in a first priority group and assigning an indicator value to the particulate count; wherein categorizing the particulate count further includes categorizing at least one of a total metal content, a metal content of a plurality of individual elements, and a metal content not present in a fresh lubricant; wherein the categorizing further includes categorizing at least a lubricant viscosity as a first priority group, and wherein the categorizing further includes categorizing at least one of a total acid number (TAN), a total base number (TBN), a pH level, an oxidation parameter, a lubricant additive, an anti-corrosion agent, an anti-oxidation agent, and a water content as a second priority group; and wherein the categorizing further includes categorizing at least one of a lubricant viscosity, a TAN, a TBN, a pH level, an oxidation parameter, and a water content as a first priority group.

Another aspect of the present disclosure includes a method for determining a level of a plurality of lubricant parameters present in a portion of lubricant; comparing the level of each of the plurality of lubricant parameters to a threshold value corresponding to each of the plurality of lubricant parameters; analyzing a priority of each of the lubricant parameters; and determining a health status of the lubricant in response to the comparing and the analyzing.

Refining aspects include the threshold value further comprising a threshold range, the threshold range including a plurality of values; wherein the analyzing further includes assigning a criticality to each of the plurality of lubricant parameters, wherein the criticality of each of the plurality of lubricant parameters is determined in response to an impact each of the lubricant parameters has on at least one of a lubricant performance and a component wear; wherein determining the level of a plurality of lubricant parameters further includes determining the level of at least one of a lubricant viscosity, a total acid number (TAN), a total base number (TBN), a pH level, an oxidation parameter, a lubricant additive, an anti-corrosion agent, an anti-oxidation agent, a water content, and a zinc content; determining at least one of a lubricant remaining useful life, a maintenance schedule, a maintenance service interval, and a maintenance service to be performed in response to the health status of the lubricant; determining a current particulate level; comparing the current particulate level to a threshold particulate level; and determining a mechanical health status in response to the comparing; and generating at least one of a maintenance schedule, a maintenance service interval, and a maintenance service to be performed in response to the mechanical health status.

Another aspect of the present disclosure includes a method receiving a sample of lubricant from an air compression system, wherein the lubricant is of a type suitable for use within the air compression system; determining a current level of a plurality of lubricant parameters present in the sample of lubricant; comparing the current level of each of the plurality of lubricant parameters to a threshold value corresponding to each of the plurality of lubricant parameters; assigning a criticality to each of the plurality of lubricant parameters, wherein the criticality of each of the plurality of lubricant parameters is determined in response to an effect each of the lubricant parameters has on at least one of a lubricant performance and a component wear; and determining a health status of the lubricant in response to the comparing and the assigning.

Refining aspects include determining at least one of a remaining lubricant useful life, a maintenance interval, a maintenance schedule, and a maintenance service in response to the health status of the lubricant; generating a health status report, wherein the health status report indicates the health status of the lubricant as at least one of a first severity, a second severity, and a third severity, wherein the first severity is less than the second severity and the second severity is less than the third severity; decreasing a predetermined duration of time between receiving the sample and receiving a second sample to be analyzed in response to the health status report indicating the second severity; indicating a maintenance service to be performed in response to the health status report indicating the third severity.

Another aspect of the present disclosure includes a method comprising determining a plurality of lubricant parameters that at least partially define a lubricant; separating the plurality of lubricant parameters into a first priority group and a second priority group, wherein the first priority group includes parameters that are more critical to lubricant performance than the second priority group; determining a threshold value for each of the plurality of lubricant parameters, wherein the threshold value is one of a minimum level or maximum level of a lubricant constituent that defines a minimum level of lubricant performance; analyzing a sample of lubricant to determine a measured value for each of the plurality of lubricant parameters; comparing the measured value to the threshold value for each of the plurality of lubricant parameters; and indicating a health status of the lubricant in response to the comparing; wherein the health status indicates a first severity level if the measured value does not exceed the threshold value for any of the lubricant parameters in the first and second priority groups; and wherein the health status indicates a second severity level if the measured value does not exceed the threshold value for any of the lubricant parameters in the first priority group and the measured value exceeds the threshold value for at least one parameter in the second priority group; and wherein the health status indicates a third severity level if the measured value exceeds the threshold value for at least one of the lubricant parameters in the first priority group.

Refining aspects include separating the lubricant parameters into a third priority group; and measuring the lubricant parameters in the third priority group and using the measured values of the third priority group in conjunction with the measured values of the first and second priority groups to determine a health status of the lubricant; and determining a maintenance procedure in response the health status indication of a first, second or third severity level.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A method, comprising:
    categorizing each of a plurality of lubricant parameters into one of a first priority group, a second priority group or a third priority group, wherein each of the priority groups are defined by a priority level determined by a criticality of the lubricant parameters based on at least one of a lubricant performance and a component life, and wherein at least one of the priority groups include a plurality of lubricant parameters having the same priority level;
    analyzing a sample of lubricant after the categorizing of the lubricant parameters;
    assigning an indicator value to each of the lubricant parameters in response to the analyzing;
    comparing each indicator value to a respective predetermined threshold value;
    determining a health status in response to the comparing of each indicator value to the respective predetermined threshold value for parameters in each of the priority groups;
    determining at least one of a maintenance service, a maintenance schedule, and a remaining useful lubricant life in response to the health status; and
    performing a maintenance service in response to the health status.

2. The method of claim 1, wherein the predetermined threshold value is a threshold range.

3. The method of claim 1, wherein determining the health status further includes determining a lubricant health status and a mechanical health status, the lubricant health status being independent of the mechanical health status.

4. The method of claim 3, wherein determining the mechanical health status further includes categorizing a particulate count in the first priority group and assigning an indicator value to the particulate count.

5. The method of claim 4, wherein categorizing the particulate count further includes categorizing at least one of a total metal content, a metal content of a plurality of individual elements, and a metal content not present in a fresh lubricant.

6. The method of claim 1, wherein the categorizing further includes categorizing at least a lubricant viscosity in the first priority group, and wherein the categorizing further includes categorizing at least one of a total acid number (TAN), a total base number (TBN), a pH level, an oxidation parameter, a lubricant additive, an anti-corrosion agent, an anti-oxidation agent, and a water content in the second priority group.

7. The method of claim 1, wherein the categorizing further includes categorizing at least one of a lubricant viscosity, a TAN, a TBN, a pH level, an oxidation parameter, and a water content in the first priority group.

8. A method, comprising:
    determining a level of a plurality of lubricant parameters present in a portion of lubricant;
    comparing the level of each of the plurality of lubricant parameters to a respective threshold value corresponding to each of the plurality of lubricant parameters;
    assigning each of the lubricant parameters to one of a first priority group, a second priority group and a third priority group, each of the priority groups defined by a priority, wherein at least one of the priority groups includes a plurality of parameters having the same defined priority;
    analyzing the priority and the level of each of the lubricant parameters after assigning each of the lubricant parameters to a priority group;
    determining a health status of the lubricant in response to the comparing and the analyzing of each of the lubricant parameters from at least two of the priority groups, wherein the health status of the lubricant is defined at different levels of severity depending on which of the priority groups that include a parameter value that falls outside of a corresponding respective threshold value;
    determining at least one of a lubricant remaining useful life, a maintenance schedule, a maintenance service interval, and a maintenance service to be performed in response to the health status of the lubricant; and
    performing a maintenance service when a parameter in one of the priority groups falls outside of the respective threshold value.

9. The method of claim 8, wherein the threshold value further comprises a threshold range, the threshold range including a plurality of values.

10. The method of claim 8, wherein the analyzing further includes assigning a criticality to each of the plurality of lubricant parameters, wherein the criticality of each of the plurality of lubricant parameters is determined in response to an impact each of the lubricant parameters has on at least one of a lubricant performance and a component wear.

11. The method of claim 8, wherein determining the level of a plurality of lubricant parameters further includes determining the level of at least one of a lubricant viscosity, a total acid number (TAN), a total base number (TBN), a pH level, an oxidation parameter, a lubricant additive, an anti-corrosion agent, an anti-oxidation agent, a water content, and a zinc content.

12. The method of claim 8, further including:
    determining a current particulate level;
    comparing the current particulate level to a threshold particulate level; and
    determining a mechanical health status in response to the comparing.

13. The method of claim 12, further including generating at least one of a maintenance schedule, a maintenance service interval, and a maintenance service to be performed in response to the mechanical health status.

14. A method, comprising:
    receiving a sample of lubricant from an air compression system, wherein the lubricant is of a type suitable for use within the air compression system;

determining a current level of a plurality of lubricant parameters present in the sample of lubricant;

assigning each of the lubricant parameters to one of a first priority group, a second priority group and a third priority group, each group having a different defined priority, wherein at least one of the priority groups includes a plurality of parameters;

comparing the current level of each of the plurality of lubricant parameters to a respective threshold value corresponding to each of the plurality of lubricant parameters after the assigning of each of the lubricant parameters to a priority group;

assigning a different criticality to each of the plurality of priority groups, wherein the criticality of each of the plurality of priority groups is determined in response to an effect each of the lubricant parameters has on at least one of a lubricant performance and a component wear;

determining a health status of the lubricant in response to the comparing and the assigning, wherein the health status is defined as one of a first severity, a second severity or a third severity depending on which of the plurality of priority groups includes a parameter with a current level falling outside of the corresponding respective threshold value;

generating a health status report, wherein the health status report indicates the health status of the lubricant as at least one of the first severity, the second severity, and the third severity, wherein the first severity is less than the second severity and the second severity is less than the third severity; and performing a maintenance service based on the health status of the lubricant.

15. The method of claim 14, further including determining at least one of a remaining lubricant useful life, a maintenance interval, a maintenance schedule, and a maintenance service in response to the health status of the lubricant.

16. The method of claim 14, further including decreasing a predetermined duration of time between receiving the sample and receiving a second sample to be analyzed in response to the health status report indicating the second severity.

17. The method of claim 14, further including indicating a maintenance service to be performed in response to the health status report indicating the third severity.

18. A method comprising:

determining a plurality of lubricant parameters that at least partially define a lubricant;

separating the plurality of lubricant parameters into one of a first priority group and a second priority group, wherein the first priority group includes a plurality of parameters that are more critical to lubricant performance than the parameters in the second priority group, wherein each of the plurality of lubricant parameters in their respective first and second priority groups have the same priority level;

determining a threshold value for each of the plurality of lubricant parameters, wherein the threshold value is one of a minimum level or maximum level of a lubricant constituent that defines a minimum level of lubricant performance, wherein each of the plurality of lubricant parameters have a different threshold value;

analyzing a sample of lubricant to determine a measured value for each of the plurality of lubricant parameters after the separating of each of the lubricant parameters into one of the first and second priority groups;

comparing the measured value to the respective threshold value for each of the plurality of lubricant parameters; and indicating a health status of the lubricant in response to the comparing;

wherein the health status indicates a first severity level if the measured value does not exceed the threshold value for any of the lubricant parameters in the first and second priority groups; and wherein the health status indicates a second severity level if the measured value does not exceed the threshold value for any of the lubricant parameters in the first priority group and the measured value exceeds the threshold value for at least one parameter in the second priority group;

wherein the health status indicates a third severity level if the measured value exceeds the threshold value for at least one of the lubricant parameters in the first priority group;

determining a maintenance procedure in response to the health status indication of a first, second or third severity level; and performing a maintenance service in response to the health status indication.

19. The method of claim 18 further comprising:

separating the lubricant parameters into a third priority group; and measuring the lubricant parameters in the third priority group and using the measured values of the third priority group in conjunction with the measured values of the first and second priority groups to determine a health status of the lubricant.

* * * * *